United States Patent [19]

Fleming

[11] Patent Number: Plant 7,524

[45] Date of Patent: May 14, 1991

[54] KALANCHOE PLANT NAMED LITTLE FLAME

[75] Inventor: Margaret M. Fleming, Soquel, Calif.

[73] Assignee: The Plant Company, Soquel, Calif.

[21] Appl. No.: 385,161

[22] Filed: Jul. 26, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A kalanchoe plant named Little Flame particularly characterized by its bright, clear red flower color; flower diameter of 13 to 15 mm at maturity; flowering response, from 10 weeks in summer to 12 weeks in winter after start of short days; very floriferous with excellent display of many flowers; excellent keeping quality of flowers and foliage; excellent branching with or without pinching; compact plant habit with small foliage; and recommended for flowering in 10 cm pots and smaller.

2 Drawing Sheets

The present invention relates to a new and distinctive cultivar of kalanchoe plant, botanically known as *Kalanchoe blossfeldiana* Poelln., and referred to by the cultivar name Little Flame.

Little Flame, identified as 586-030, is a product of a planned breeding program which had the objective of creating new kalanchoe cultivars for year-round commercial production having an earlier flowering response, well branched yet compact flowering plants, and good flower and foliage keeping quality.

Little Flame was originated by the inventor Margaret M. Fleming from a controlled selfing of the parent plant, an unnamed seedling identified as 403-253, (now referred to by the varietal designation Western Red, disclosed in pending plant application Ser. No. 385,163 by the present inventor, in Half Moon Bay, Calif., in 1984.

Little Flame was discovered and selected as one flowering plant within the progeny of the stated selfing by Margaret M. Fleming in February of 1986 in a controlled environment in Soquel, Calif.

The first act of asexual reproduction of Little Flame was accomplished when vegetative cuttings were taken from the initial selection in July of 1986 in a controlled environment in Soquel, Calif., by Margaret M. Fleming.

Horticultural examination of controlled flowerings of successive plantings has shown that the unique combination of characteristics as herein disclosed for Little Flame are firmly fixed and are retained through successive generations of asexual reproduction.

Little Flame has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Little Flame, which, in combination, distinguish this kalanchoe as a new and distinct cultivar:

1. Bright, clear red flower color.
2. Flower diameter of 13–15 mm at maturity.
3. Flowering response of from 10 weeks in summer to 12 weeks in winter, from start of short day treatments.

4. Very floriferous with excellent display of many flowers.
5. Excellent keeping quality of flowers and foliage.
6. Excellent branching with or without pinching.
7. Compact plant habit, with small foliage.
8. Recommended for flowering in 10 cm pots and smaller.

The accompanying colored photographic drawings show typical inflorescence and leaf characteristics of Little Flame, with colors being as nearly true as possible with illustrations of this type.

Sheet 1 is a color photograph showing in perspective view a plant of Little Flame grown as a non-pinched flowering kalanchoe in a 10 cm pot.

Sheet 2 is a black and white photograph showing the leaves of Little Flame at three stages of development (mature, intermediate and immature).

Of the commercial cultivars known to the inventor, the most similar in comparison to Little Flame are the cultivars identified as Attraction, disclosed in U.S. Plant Pat. No 5,888, and Pollux, disclosed in U.S. Plant Pat. No. 4,816. In comparision to Attraction, Little Flame has a slightly smaller flower diameter, better flower color and better keeping quality of flowers and foliage. Attraction often shows an early breakdown of lower foliage, while Little Flame does not exhbit this foliar breakdown. Similar traits are the compact plant habit, flowering response and branching habit. In comparison to Pollux, Little Flame has a much faster flowering response, by two to three weeks, and much better resistance to mildew. Little Flame has a much higher productivity as a stock plant in cutting production than Pollux. Similar traits are flower color and size, compact plant habit, and form and color of the foliage.

In comparison to the parent cultivar Western Red, the color of Western Red is a deeper shade of red than Little Flame. Little Flame is more compact in habit, has smaller foliage, smaller flowers, and a response of 10–12 weeks from the start of short day treatment. Both Little Flame and Western Red have shown resistance to flower and foliar diseases, and both have relatively long lasting flowers.

A further comparison can be made between the present cultivar and Cinnabar, the female parent of Western Red. The flower color of Cinnabar is more of an orange-red compared with the red color of Little Flame. Cinnabar blooms a week earlier than Little Flame, but the keeping quality of the flowers of Little Flame is much better. The flowers of Little Flame are smaller in diameter, but more abundant. In addition, the leaves of Little Flame are smaller, more durable, darker green, and much less likely to degrade than the leaves of Cinnabar.

In the following description color references are made to The Royal Horticultural Society Colour Chart. The very bright red color of the upper surface of the petals is not represented in the R.H.S. Colour Chart, and the color values given are those closest to the actual color of Little Flame. The color values were determined on plant material grown as a non-pinched pot plant in a 10 cm pot in Soquel, Calif., on Oct. 23, 1988.

Classification:

*Botanical.*—*Kalanchoe blossfeldiana* Poelln. cv. Little Flame.

*Commercial.*—Flowering pot kalanchoe.

Parentage:

A controlled selfing of an unnamed seedling, identified as 403-253 now identified as Western Red.

Propagation:

(A) *Type cutting.*—Short tip cutting, with stems up to 2 cm.

(B) *Time to root.*—10 days at 21° C. in summer, 14 days at 21° in winter.

(C) *Rooting habit.*—Many very fine roots, fibrous.

Plant Description:

(A) *Form.*—Short, compact, upright growth. Growing and scheduling practices can produce a small plant in a 10 cm pot and smaller pot.

(B) *Habit of growth*—Rate of growth slow for this type of plant, with 1-3 applications of 3500 ppm B-9 SP growth regulation being the preferred regimen. Generally, shoots are formed at every node. Height of plant above 10 cm. pot is 13-18 cm; internode length of vegetative natural plant is 12-25 mm.

(C) *Foliage description.*—Leaves simple, opposite, slightly lobed. 1. Size: Average full grown leaf in a 10 cm flowering pot is small: 100 mm long×45 mm wide. 2. Shape: Ovate to elliptic, apex obtuse to slightly pointed, base attenuate. 3. Texture: Glabrous, coriaceous, succulent. 4. Margin: Sinuate to crenate. 5. Color: Mature foliage: Upper surface 137A to 137B. Under surface 138B to 138C. 6. Durability: Excellent, no degradation observed, even on the lower foliage of plants retained for months beyond normal expectancy.

Flowering Description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (each of which is 10-15 mm. in length) will continue for two months or more. Individual flowers last two weeks or more after opening.

(B) *Flowering response.*—Flowering time under controlled daylength after start of short days is 10 weeks in summer to 12 weeks in winter.

(C) *Flowers borne.*—Compound dichasial cymes; peduncle length 5-10 cm., diameter 3-7 mm.; pedicel length 4-6 mm., diameter less than 1.0 mm.

(D) *Quantity of flowers.*—Highly floriferous, with up to 100 flowers per major inflorescence and 500 or more flowers per plant in a 10 cm. pot produced in accordance with commercial culture; high number of flowers on both main axis and side laterals, with 4 to 6 side laterals in a 10 cm pot.

(E) *Petals.*—1. Shape: Slightly pointed to almost round. 2. Color: Upper surface: Between 40A and 43A. Under surface: Base 38A, heavily streaked with 41B. 3. Number of petals: 4, united in corolla. 4. Flower diameter: 13 to 15 mm at maturity.

(F.) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, size 4 mm long, color light green.

(G) *Keeping qualities.*—Excellent; each flower lasts two weeks or more under normal conditions of finishing and holding.

Disease Resistance:

Resistant to Botrytis and Powdery Mildew; to date, chlorosis, necrotic spots, stem rot, or root rot have not been observed, and Little Flame has been trouble free.

Fragrance:

No perceptible fragrance of flowers or foliage.

I claim:

1. A new and distinct plant of kalanchoe named Little Flame, as described and illustrated.

* * * * *

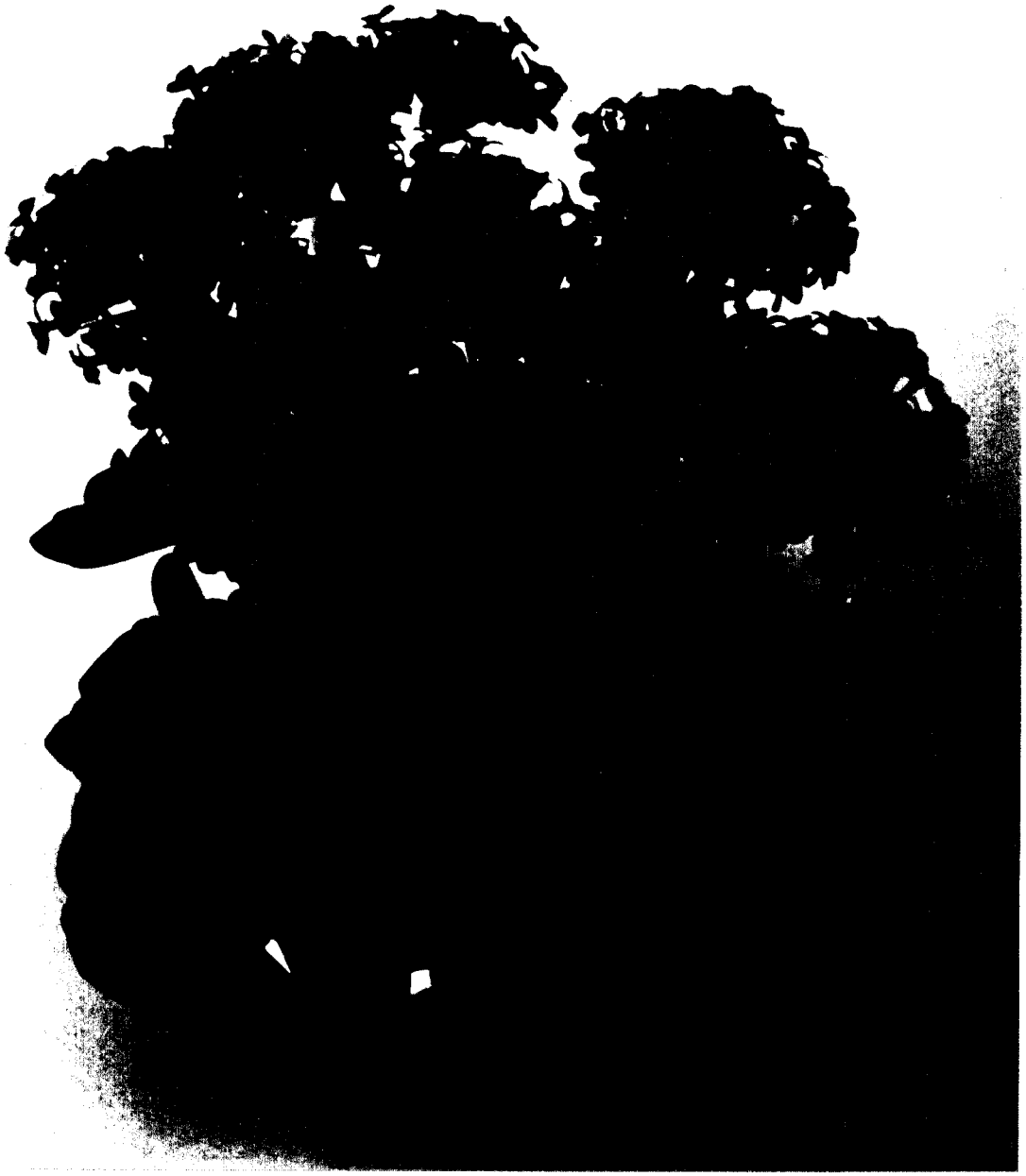

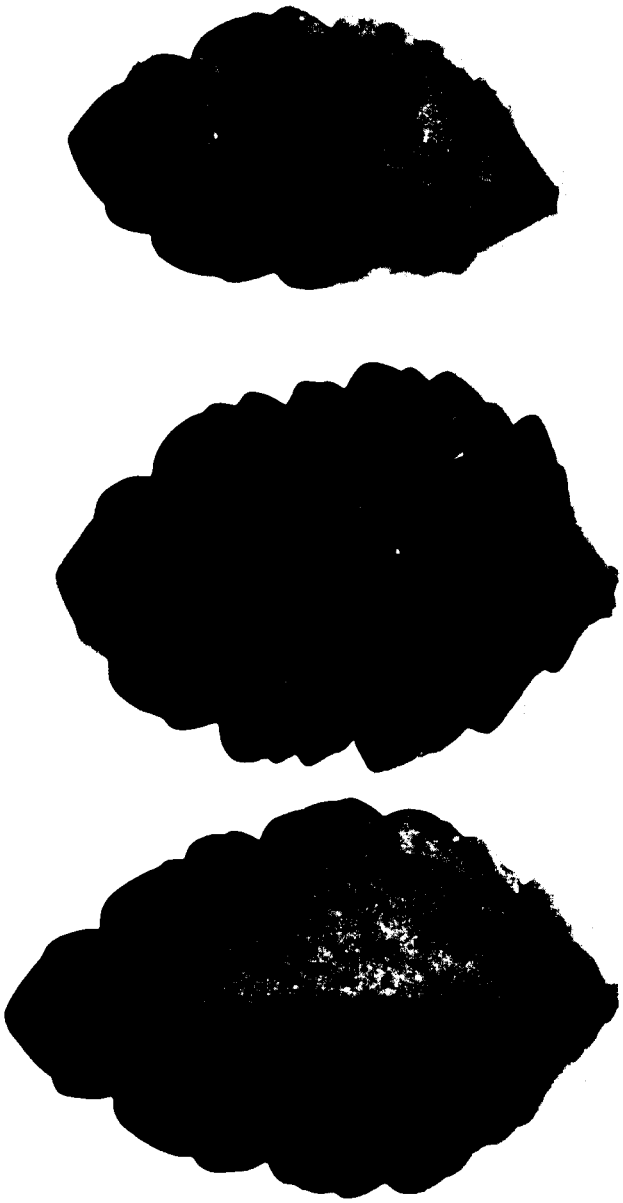
LITTLE FLAME